United States Patent
Seo (10) Patent No.: US 9,314,309 B2
(45) Date of Patent: Apr. 19, 2016

(54) SURGICAL ROBOT AND METHOD OF CONTROLLING THE SAME

(71) Applicant: SAMSUNG ELECTRONICS CO., LTD., Suwon-si (KR)

(72) Inventor: Kee Hong Seo, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 309 days.

(21) Appl. No.: 14/031,580

(22) Filed: Sep. 19, 2013

(65) Prior Publication Data

US 2014/0276940 A1    Sep. 18, 2014

(30) Foreign Application Priority Data

Mar. 13, 2013    (KR) .................. 10-2013-0026616

(51) Int. Cl.
*G06F 19/00* (2011.01)
*A61B 19/00* (2006.01)

(52) U.S. Cl.
CPC ......... *A61B 19/2203* (2013.01); *A61B 19/5202* (2013.01); *A61B 19/5212* (2013.01); *A61B 2019/2223* (2013.01); *A61B 2019/5265* (2013.01); *Y10S 901/47* (2013.01)

(58) Field of Classification Search
CPC ........... A61B 19/2203; A61B 19/5202; A61B 19/5212; A61B 1/0008; Y10S 901/47
USPC ......... 700/245, 248, 253, 254, 257, 258, 260; 359/201.1; 385/15; 606/130; 901/47
See application file for complete search history.

(56) References Cited

U.S. PATENT DOCUMENTS

| | | | |
|---|---|---|---|
| 6,587,750 B2 * | 7/2003 | Gerbi ..................... | A61B 19/22 128/897 |
| 6,594,552 B1 * | 7/2003 | Nowlin ................... | A61B 19/22 318/568.11 |
| 6,684,129 B2 * | 1/2004 | Salisbury, Jr. .......... | A61B 19/22 128/897 |
| 7,142,945 B2 * | 11/2006 | Wang ....................... | B25J 5/007 318/568.11 |
| 7,155,316 B2 * | 12/2006 | Sutherland ............. | A61B 19/22 318/568.11 |
| 9,161,684 B2 * | 10/2015 | Seibel .................. | A61B 1/0008 |
| 2004/0264853 A1 * | 12/2004 | Schwarz .............. | A61N 5/0601 385/31 |
| 2014/0263172 A1 * | 9/2014 | Xie .......................... | G03F 7/36 216/41 |

FOREIGN PATENT DOCUMENTS

| | | |
|---|---|---|
| JP | 2009-273521 | 11/2009 |
| KR | 10-2010-0123160 | 11/2010 |
| KR | 10-2011-0118640 | 10/2011 |
| WO | WO 2010/078016 | 7/2010 |

OTHER PUBLICATIONS

Lai et al., Evaluating Control Modes for Constrained Robotic Surgery, 2000, IEEE, p. 603-609.*
Ghodoussi et al., Robotic Surgey—The Transatlantic Case, 2002, IEEE, p. 1882-1888.*
Mack, Minimally Invasive and Robotic Surgery, 2001, IEEE, p. 568-572.*

* cited by examiner

*Primary Examiner* — McDieunel Marc
(74) *Attorney, Agent, or Firm* — Harness, Dickey & Pierce, P.L.C.

(57) ABSTRACT

A surgical robot including a slave device performing a surgical operation upon a patient and a master device controlling the surgical operation of the slave device. The slave device includes an image capture unit including a first lighting unit radiating visible light, a second lighting unit radiating UV light, and a camera capturing a visible-light image and a surgical tool coated with a UV reactive material emitting light in response to UV light radiated by the second lighting unit.

12 Claims, 8 Drawing Sheets

SURGICAL ROBOT AND METHOD OF CONTROLLING THE SAME

CROSS-REFERENCE TO RELATED APPLICATIONS

This application claims the benefit of Korean Patent Application No. 10-2013-0026616, filed on Mar. 13, 2013 in the Korean Intellectual Property Office, the disclosure of which is incorporated herein by reference.

BACKGROUND

1. Field

Embodiments of the present disclosure relate to a surgical robot capable of efficiently separating surgical tools from a background image acquired by a camera and a method of controlling the same.

2. Description of the Related Art

Minimally invasive surgery generally refers to surgery capable of minimizing incision size and recovery time. Minimally invasive surgery is different from laparotomy, which uses relatively large surgical incisions through a part of the human body (e.g., the abdomen). In minimally invasive surgery, after forming at least one small incision hole (or invasive hole) of 0.5 cm to 1.5 cm through the abdominal wall, an operator inserts an endoscope and surgical tools through the incision hole, to perform surgery while viewing images provided by the endoscope.

In comparison with laparotomy, minimally invasive surgery causes less post-operative pain, faster recovery of bowel movement, earlier restoration of ability to eat, shorter hospitalization, faster return to daily life, and better cosmetic effects owing to the small incision size. Due to these properties, minimally invasive surgery is used for cholecystectomy, prostatic carcinoma surgery, hernia repair, hysterectomy, and the like, and applications thereof continue to grow.

In general, a surgical robot used in minimally invasive surgery includes a master device and a slave device. The master device generates a control signal in accordance with manipulation performed by a doctor and transmits the control signal to the slave device. The slave device receives the control signal from the master device and performs manipulation required for surgery on a patient. The master device and the slave device may be integrated, or may be separately arranged in an operating room.

The slave device includes at least one robot arm. A surgical tool is mounted on an end of the robot arm and inserted into a human body to perform a surgical operation at a surgical region in a patient in accordance with a control signal received from the master device. Thus, in such minimally invasive surgery and laparoscopic surgery using a surgical robot, the position of the surgical tool inserted into the patient needs to be accurately detected to control the operation of the surgical tool.

SUMMARY

Therefore, it is an aspect of the present disclosure to provide a surgical robot capable of accurately estimating location information of a surgical tool inserted into a patient's body and a method of controlling the same.

Additional aspects of the disclosure will be set forth in part in the description which follows and, in part, will be obvious from the description, or may be learned by practice of the disclosure.

In accordance with one aspect of the present disclosure, a surgical robot includes a slave device performing a surgical operation upon a patient and a master device controlling the surgical operation of the slave device. The slave device includes an image capture unit including a first lighting unit radiating visible light, a second lighting unit radiating UV light, and a camera capturing a visible-light image and a surgical tool coated with a UV reactive material emitting light in response to UV light radiated by the second lighting unit.

In accordance with another aspect of the present disclosure, a method of controlling a surgical robot including a slave device performing a surgical operation upon a patient and a master device controlling the surgical operation of the slave device includes performing a surgical operation by inserting a surgical tool coated with a UV reactive material into a patient's body, radiating visible light and UV light into the patient's body, acquiring a first image during visible light radiation and a second image during UV radiation, and calculating position and direction of the surgical tool using the acquired first image and second image.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

The aspects, particular advantages and novel features of the embodiments of the present disclosure will become apparent with reference to the following detailed description and embodiments described below in detail in conjunction with the accompanying drawings. In the drawings, the same or similar elements are denoted by the same reference numerals even though they are depicted in different drawings. In the following description of the embodiments, a detailed description of known functions and configurations incorporated herein will be omitted when it may make the subject matter of the embodiments rather unclear. Herein, the terms first, second, etc. are used simply to discriminate any one element from other elements, and the elements should not be limited by these terms.

Hereinafter, embodiments of the present disclosure will be described in detail with reference to the accompanying drawings.

Figure 1:
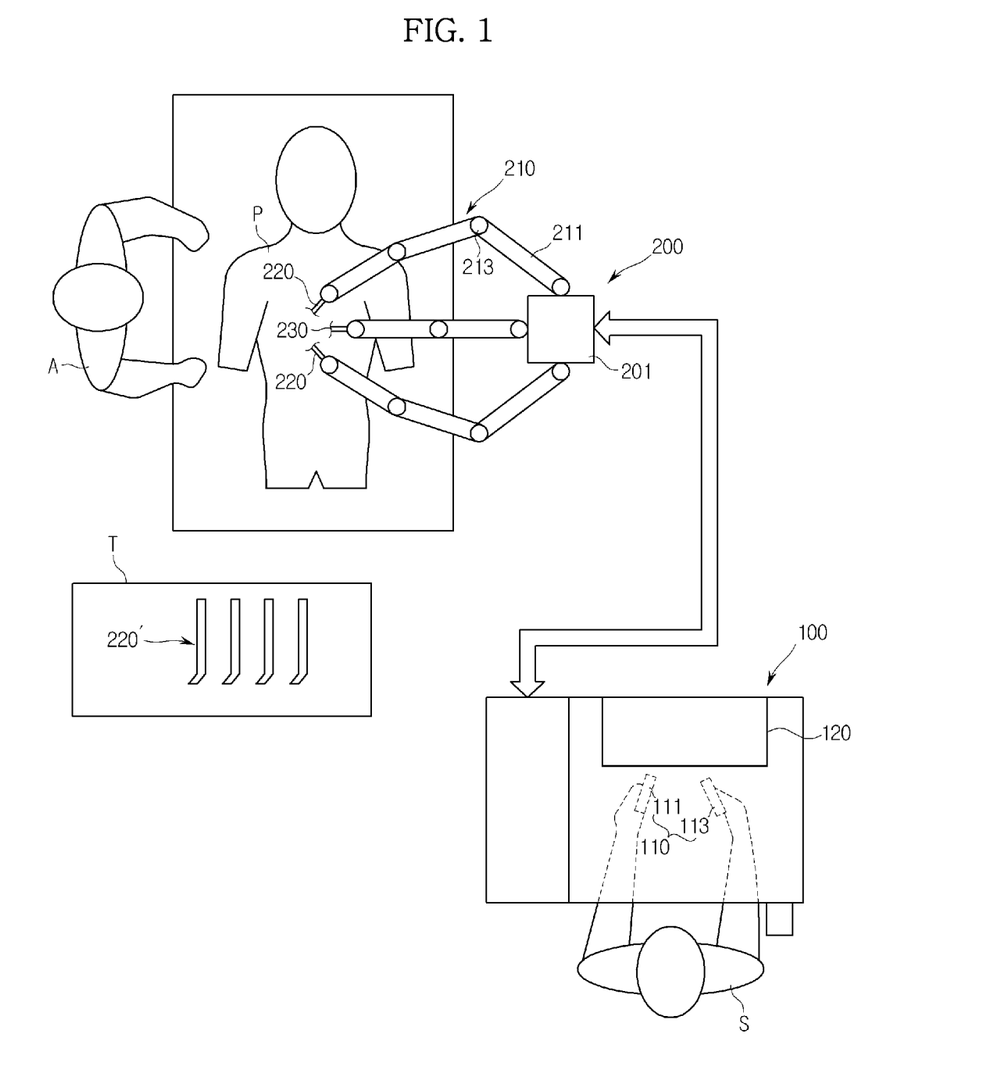
FIG. 1 is a diagram illustrating an outer appearance of a surgical robot.
Figure 2:
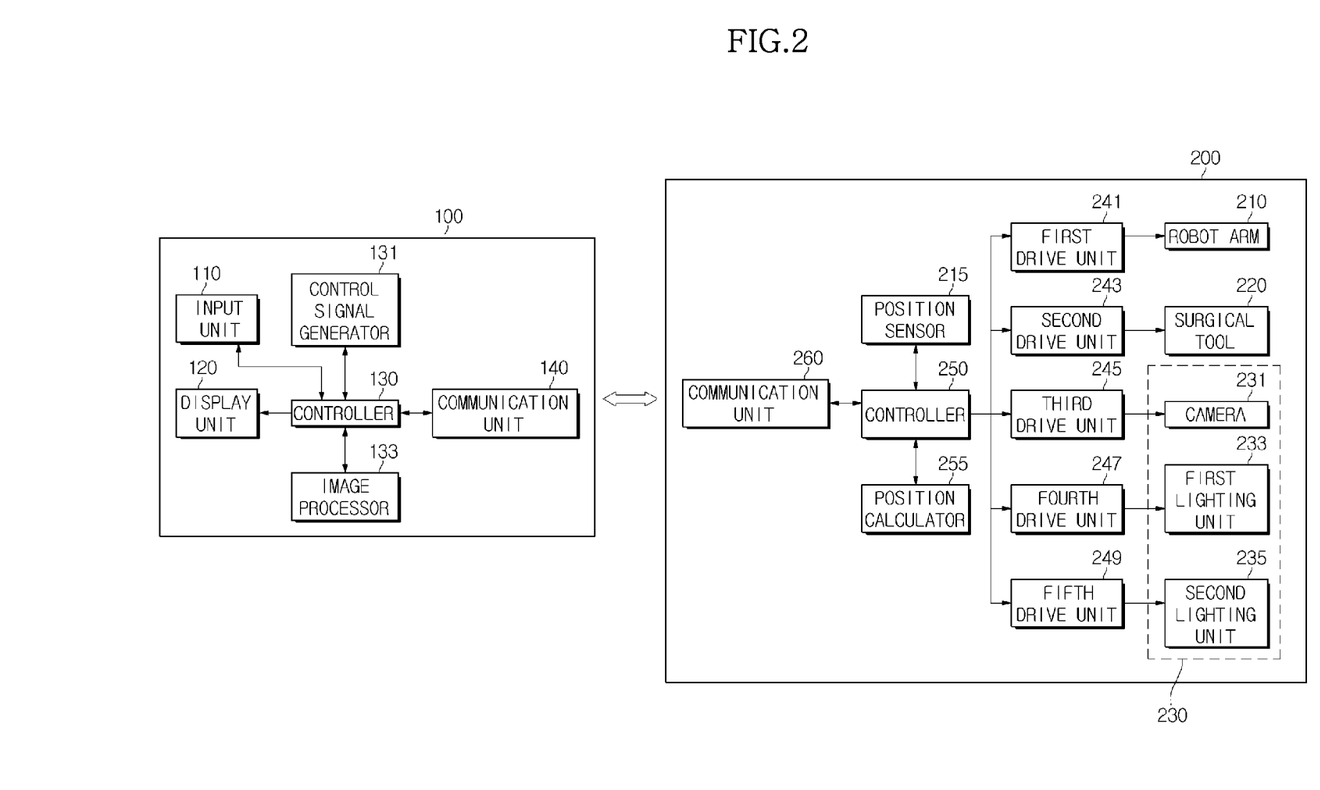
FIG. 2 is a block diagram illustrating constituent elements of a surgical robot.

FIG. 1 is a diagram illustrating an outer appearance of a surgical robot. FIG. 2 is a block diagram illustrating constituent elements of a surgical robot.

A surgical robot may include a slave device 200 to perform surgery on a patient P who lies on an operating table, and a master device 100 to remotely control the slave device 200 in accordance with manipulation by an operator S (e.g., a doctor). In this regard, at least one assistant A assisting the operator S may be positioned near the patient P.

Here, assisting the operator S may refer to assisting a surgical operation performed in accordance with manipulation by the operator S while surgery is in progress, such as replacing surgical tools, but is not limited thereto. For example, a variety of surgical tools may be used according to the surgical operation. Since the number of robot arms 210 of the slave device 200 is limited, the number of surgical tools mounted thereon at one time is also limited. Accordingly, when the surgical tool needs to be changed out during surgery, the operator S instructs the assistant A, positioned near the patient P, to change out the surgical tool. In accordance with the instruction, the assistant A removes a surgical tool 220 that is no longer needed from the robot arm 210 of the slave device 200 and mounts another surgical tool 220' placed on a tray T on the corresponding robot arm 210.

The master device 100 and the slave device 200 may be separately constructed as physically independent devices, without being limited thereto. For example, the master device 100 and the slave device 200 may also be integrated with each other as a single device enclosed within a single physical package.

As illustrated in FIGS. 1 and 2, the master device 100 may include, for example, an input unit 110 and a display unit 120.

The input unit 110 refers to an element that receives an instruction for selection of an operation mode of the surgical robot or an instruction for remote control of operations of the robot arm 210, the surgical tools 220, and the image capture unit 230 of the slave device 200 which are input by the operator S. In the present embodiment, the input unit 110 may include a haptic device, a clutch pedal, a switch, and a button, but is not limited thereto. For example, a voice recognition device may be used. Hereinafter, a haptic device will be exemplarily described as an example of the input unit 110, but a variety of devices may also be used as the input unit 110.

FIG. 1 exemplarily illustrates that the input unit 110 includes two handles 111 and 113, but the present embodiment is not limited thereto. For example, the input unit 110 may include one handle or three or more handles as well.

The operator S respectively manipulates two handles 111 and 113 using both hands as illustrated in FIG. 1 to control operation of the robot arm 210 of the slave device 200. That is, upon manipulation of the input unit 110 by the operator S, a controller 130 may generate a control signal corresponding to status information of the manipulated input unit 110 using a control signal generator 131 and may transmit the generated control signal to the slave device 200 through a communication unit 140.

The display unit 120 of the master device 100 may display a real image of the inside of the patient P's body acquired by the image capture unit 230, a 3D image generated using a medical image of the patient P before surgery, and the like. To this end, the master device 100 may include an image processor 133 to process image data received from the slave device 200 and to output processed image information to the display unit 120. In this regard, "image data" may include a real image acquired by the image capture unit 230, a 3D image generated using a medical image of the patient P before surgery, or a combination thereof, and the like, as described above, but is not limited thereto.

The display unit 120 may include at least one monitor, and each monitor may be implemented to individually display information required for surgery. For example, when the display unit 120 includes three monitors, one of the monitors may display the real image acquired by the image capture unit 230, a 3D image generated using a medical image of the patient P before surgery, and the like, and the other two monitors may respectively display information regarding operation status of the slave device 200 or information about the patient P. In this regard, the number of monitors may vary according to the type, kind, or amount of information to be displayed.

Here, "information of the patient" may refer to information indicating vital signs of the patient, for example, bio-information such as body temperature, pulse, respiration, and blood pressure. In order to provide such bio-information to the master device 100, the slave device 200, which will be described later, may further include a bio-information measurement unit including a body temperature-measuring module, a pulse-measuring module, a respiration-measuring module, an oxygen saturation-measuring module, a blood pressure-measuring module, and the like. To this end, the master device 100 may further include a signal processor (not shown) to receive bio-information from the slave device 200, process the bio-information, and output the resultant information to the display unit 120.

As illustrated in FIG. 1, the slave device 200 may include a plurality of robot arms 210, various surgical tools 230 mounted on ends of the robot arms 210, and the image capture unit 230.

The robot arms 210 may be coupled to a body 201 in a fixed state and supported thereby as illustrated in FIG. 1. In this regard, the quantity of surgical tools 230 and robot arms 210 used at once may vary according to various factors, such as diagnostic methods, surgical methods, and spatial limitations of an operating room.

In addition, each of the robot arms 210 may include a plurality of links 211 and a plurality of joints 213. Each of the joints 213 may connect links 211 and may have 1 degree of freedom (DOF) or greater. Here, "degree of freedom (DOF)" refers to a DOF with regard to kinematics or inverse kinematics. A DOF of a mechanism indicates the number of independent motions of a mechanism or the number of variables that determine independent motions at relative positions between links. For example, an object in a 3D space defined by X, Y, and Z-axes has at least one DOF selected from the group made up of 3 DOFs to determine a spatial position of the object (a position on each axis), 3 DOFs to determine a spatial orientation of the object (a position on each axis), and 3 DOFs to determine a spatial orientation of the object (a rotation angle relative to each axis). More specifically, it will be appreciated that when an object is movable along each of X-, Y-, and Z-axes and is rotatable about each of X-, Y-, and Z-axes, that the object has 6 DOF.

In addition, a detector (not shown) that may detect information indicating the state of the joint 213 may be mounted on the joint 213. For example, the detector may include a force/torque detector that detects force/torque information applied to the joint 213, a position detector that detects position information of the joint 213, and a speed detector that detects speed information of the joint 213. In an embodiment, the speed detector may be dispensed with according to the type of position sensor used as the position detector. FIG. 2 illustrates the position sensor used as the position detector only. However, the force/torque detector and the speed detector may also be applied thereto.

The position sensor 215 may be a potentiometer, an encoder, or the like, but is not limited thereto. The position sensor 215 may be mounted on each joint 213 of the robot arm 210, may detect information regarding the status of motion of each joint 213 of the robot arm 210 as described above, and may transmit the information to a controller 250. The controller 250 that receives the detected information regarding the status of motion of each joint 213 of the robot arm 210 from the position sensor 215 may calculate current position and direction of the surgical tools 220 mounted at one end of the robot arm 210 using a position calculator 255. In this regard, the position calculator 255 applies the input information to kinematics of the robot arm 210 to calculate the current position and direction of the surgical tools 220. However, this is an exemplary embodiment, and the calculation method of the position calculator 255 is not limited thereto.

As illustrated in FIG. 2, the slave device 200 may further include a first drive unit 241 to control motion of the robot arm 210 according to the control signal received from the master device 100.

For example, when the operator S manipulates the input unit 110 of the master device 100, the controller 130 of the master device 100 generates a control signal corresponding to the status information of the manipulated input unit 110 and transmits the control signal to the slave device 200, and the controller 250 of the slave device 200 drives the first drive unit 241 in accordance with the control signal received from the master device 100 to control motion of each joint of the robot arm 210 so as to operate the robot arm 210. Here, a substantial control process of, for example, rotating and moving the robot arm 210 in accordance with the manipulation of the input unit 110 by the operator S need not fall within the scope of the present disclosure and thus a detailed description thereof will not be given.

Meanwhile, each joint of the robot arm 210 of the slave device 200 may move according to the control signal received from the master device 100 as described above. However, the joint may also move by external force. That is, the assistant A positioned near the operating table may manually move each of the joints of the robot arm 210 to control location, orientation, and the like of the robot arm 210.

Although not illustrated in detail in FIG. 1, each of the surgical tools 220 may include a housing mounted on one end of the robot arm 210, a shaft extending from the housing by a predetermined length, and an end effector mounted on one end of the shaft.

In general, the surgical tools 220 may be classified into main surgical tools and auxiliary surgical tools. Here, "main surgical tools" may refer to surgical tools including end effectors which perform direct surgical motion, such as cutting, suturing, cauterizing, and rinsing, on the surgical region. Examples of the end effector may include a scalpel, surgical needle, clamps, a grasper, scissors, a stapler, a needle holder, a scalpel, a cutting blade, and the like, but is not limited thereto. Any instruments required for surgery may also be used.

"Auxiliary surgical tools" may refer to surgical tools including end effectors, such as a skin holder, which do not perform direct motions on the surgical region but rather assist motion of the main surgical tools.

In addition, a drive wheel may be coupled to the housing. The end effector may be driven by connecting the drive wheel with the end effector via wire or the like and rotating the drive wheel. To this end, a second drive unit 243 to rotate the drive wheel may be mounted on one end of the robot arm 210. For example, upon manipulation of the input unit 110 of the master device 100 by the operator S, the master device 100 generates a control signal corresponding to status information of the manipulated input unit 110 and transmits the control signal to the slave device 200, and the controller 250 of the slave device 200 drives the second drive unit 243 in accordance with the control signal received from the master device 100, so as to control the end effector in a desired manner.

However, the operating mechanism of the end effector is not necessarily constructed as described above, and various other electrical/mechanical mechanisms to realize required motions of the end effector for robot surgery may also be applied thereto.

In addition, the surgical tool 220 of the slave device 200 according to the present embodiment may be coated with a UV reactive material that emits light in response to UV light. Here, "UV reactive material" refers to a material that is invisible under visible light but emits visible light when exposed to UV light.

Generally, light is not produced inside the human body. In order to efficiently perform surgical operation, light is radiated into the patient P's body. Here, light radiated into the patient P's body is visible light having a wavelength range visible to human eyes. As described above, when visible light is radiated into the patient P's body, all of organs and tissues of the patient P and the surgical tools 220 inserted into the patient P's body become visible to human eyes.

Meanwhile, when UV light is radiated into the patient P's body, the inside of the patient P's body is not visible since UV light has a wavelength range invisible to the human eye. However, according to the illustrated embodiment, since the UV reactive material coated on the surgical tool 220 emits light having a visible wavelength range in response to the radiated UV light, the surgical tool 220 is visible to the human eyes. That is, when UV light is radiated into the inside of the patient P's body, organs and tissues around the surgical region of the patient P are not visible, but the surgical tool 220 is visible due to emission of light by the UV reactive material.

Accordingly, when an image of the inside of the patient P's body is acquired through the camera 231, which will be described later, an image in which only the surgical tool 220 is visible without displaying organs and tissues around the surgical region of the patient P may be obtained.

In general, a current position and direction of the surgical tool 220 that is inserted into the patient P's body to perform the surgery may be estimated by matching information calculated through the following two methods. First, the current position and direction of the surgical tool 220 may be calculated by attaching the position sensor 215 to the joint of the robot arm 210 provided with the surgical tool 220 and applying the status information of the joint of the robot arm 210 detected through the position sensor 215 to kinematics. Second, the surgical tool 220 is separated from the background image acquired by the camera, and the position and direction of the separated surgical tool 220 are calculated.

In this regard, in order to efficiently separate the surgical tool 220 from the background image according to the second method, a marker is attached to the surgical tool 220. The marker may affect an appearance of the surgical tool 220 and may not be recognized since the marker may be attached to a portion of the surgical tool 220 that is hidden by impurities such as blood, bodily fluids, and soft tissues or another surgical tool 220.

Accordingly, according to the illustrated embodiment, UV reactive material that does not affect the appearance of the surgical tool 220 and that may be applied to the overall surface of the surgical tool 220 is used. According to the present embodiment, the UV reactive material may be applied to the overall surface or a portion of the surgical tool 220.

Here, applying the UV reactive material to the overall surface of the surgical tool 220 may refer to applying the UV reactive material to the overall surfaces of the shaft and the end effector of the surgical tool 220, without being limited thereto, or applying the UV reactive material to the overall surface of the end effector. In addition, applying the UV reactive material to a portion of the surgical tool 220 may refer to applying the UV reactive material to a portion of the shaft, a portion of the end effector, or portions of the shaft and the end effector of the surgical tool 220. Here, the UV reactive material may be coated to have a predetermined shape, without being limited thereto. In addition, when the UV reactive material is coated on a portion of the surgical tool 220, a plurality of coated regions may be formed, but the present embodiment is not limited thereto.

Furthermore, according to the illustrated embodiment, the slave device 200 of the surgical robot may include an image capture unit 230 that includes a first lighting unit 233 radiating visible light, a second lighting unit 235 radiating UV light, and a camera 231 capturing an image as illustrated in FIG. 2. Here, the first lighting unit 233, the second lighting unit 235, and the camera 231 may be integrated with each other, or may be separated as physically independent devices. In addition, a conventional surgical robot including an endoscope and a light source radiating UV light applied to the endoscope may be used. Alternatively, a conventional surgical robot including a light source separately installed from an endoscope may be used.

The first lighting unit 233 radiating visible light may be a white lighting unit, for example, a halogen lamp, a xenon lamp, or a light emitting diode (LED), but is not limited thereto. The second lighting unit 235 radiating UV light may be a UV lighting unit, for example, a UV light emitting diode (UV LED), but is not limited thereto.

The camera 231 may be a stereo camera including a pair of cameras to acquire a 3D image, i.e., a left-eye camera and a right-eye camera, but is not limited thereto. According to the illustrated embodiment, the camera 231 may also be a camera that captures a visible-light image. In this regard, "visible-light image" refers to an image visible to human eyes in a visible wavelength range and may include all images acquired under visible light and under UV light according to the present embodiment. Hereinafter, "image acquired under visible light" is referred to as "first image", and "image acquired under UV light" is referred to as "second image".

The camera 231 may also be a complementary metal-oxide Semiconductor (CMOS) camera and a charge coupled device (CCD) camera, but is not limited thereto.

As illustrated in FIG. 2, the slave device 200 according to the illustrated embodiment may include a third drive unit 245, a fourth drive unit 247, and a fifth drive unit 249 to respectively drive the camera 231, the first lighting unit 233, and the second lighting unit 235. For example, the controller 250 of the slave device 200 may respectively drive the third drive unit 245, the fourth drive unit 247, and the fifth drive unit 249 in accordance with the control signal from the master device 100 so as to operate the camera 231, the first lighting unit 233, and the second lighting unit 235.

In this regard, the controller 130 of the master device 100 may control on/off operations of the first lighting unit 233 and the second lighting unit 235 such that the first lighting unit 233 and the second lighting unit 235 alternately emit light. That is, the first lighting unit 233 and the second lighting unit 235 may alternately emit light during successive time periods. For example, the first lighting unit 233 may emit light during a first time period, the second lighting unit 235 may emit light during a second time period, the first lighting unit 233 may emit light during a third time period and so on. In an embodiment, a time period during which the first lighting unit 233 emits light may be longer than a time period during which the second lighting unit 235 emits light.

Particularly, on/off operations of the first lighting unit 233 and the second lighting unit 235 may be controlled such that a time period during which visible light is radiated is longer than a time period during which UV light is radiated. Accordingly, the operator S and assistant A performing surgery may not recognize the radiation of UV light. That is, the operator S and the assistant A performing a surgical operation need to thoroughly check the status of the inside of the patient P's body, and such checking may be possible only while visible light is radiated. While UV light is radiated, only the UV reactive material coated on the surgical tool 220 and emitting light is visible, but organs and tissues around the surgical region of the patient P are not visible. Thus, as a UV radiation time increases, the surgical tool 220 emitting light is only visible to the operator S and the assistant A, but the inside of the patient P's body cannot be observed due to lack of radiated visible light, thereby affecting the surgical operation. Thus, the controller 130 of the master device 100 may control the time period during which the second lighting unit 235 emits light to be 0.1 sec or less such that the operator S and the assistant A cannot recognize UV radiation.

Meanwhile, the controller 130 of the master device 100 may also control on/off operations of the first lighting unit 233 and the second lighting unit 235 such that the second lighting unit 235 continuously emits light, and the first lighting unit 233 periodically emits light at predetermined intervals instead of alternating radiation by the first lighting unit 233 and the second lighting unit 235 as described above.

In particular, visible light and UV light may be simultaneously radiated into the patient P's body, and then the first lighting unit 233 radiating visible light may be turned off for a short time period and then turned back on. In this regard, a radiation-off time of the first lighting unit 233 may be shorter than a radiation-on time of the first lighting unit 233. As described above, in order to prevent the operator S and the assistant A from being aware of UV radiation, the radiation-off time may be, for example, 0.1 sec or less.

When the first lighting unit 233 and the second lighting unit 235 alternately radiate visible light and UV light as described above, or when the second lighting unit 235 consistently radiates UV light and the first lighting unit 233 periodically radiates visible light at predetermined intervals, the operator S and the assistant A do not recognize UV radiation. However, the camera 231 may acquire images while only the first lighting unit 233 operates, while only the second lighting unit 235 operates, and while both the first lighting unit 233 and the second lighting unit 235 simultaneously operate. In this regard, an image acquired while visible light and UV light are simultaneously radiated respectively by the first lighting unit 233 and the second lighting unit 235 may be identical to an image acquired while radiation is performed only by the first lighting unit 233.

Figure 3:
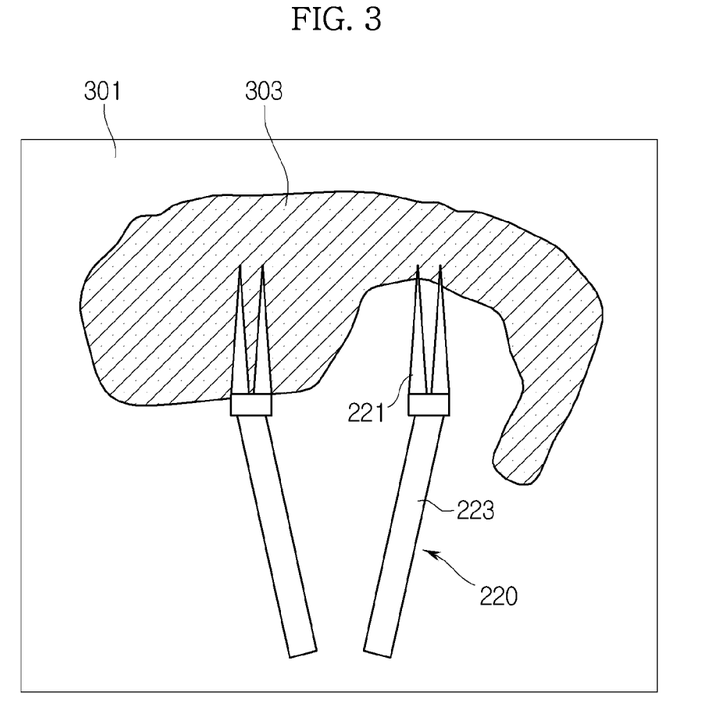
FIG. 3 is a first image acquired under visible light.

For example, an organ 303, peripheral tissues 301, and the surgical tool 220 inserted into the patient may be shown in images acquired while only the first lighting unit 233 operates and while the first lighting unit 233 and the second lighting unit 235 simultaneously operate as illustrated in FIG. 3. Meanwhile, only a portion of the surgical tool 220 coated with the UV reactive material that emits light in response to UV radiation may be shown in an image acquired while only the second lighting unit 235 operates as illustrated in FIG. 4.

Figure 4:
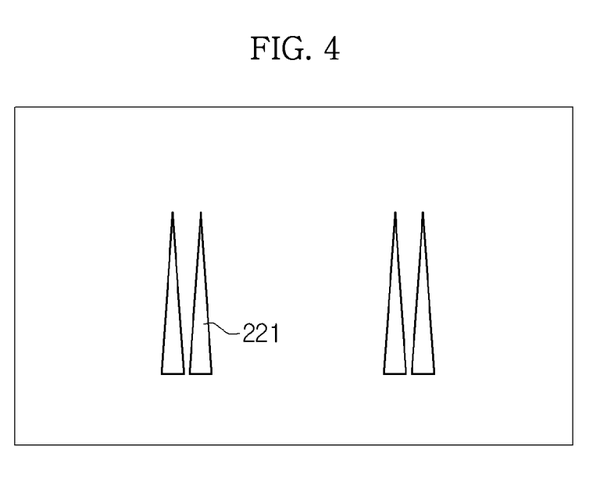
FIG. 4 is a second image acquired under UV light.

FIG. 4 exemplarily illustrates the appearance of an image in which the UV reactive material is coated over the entire surface of the end effector 221 of the surgical tool 220. However, the UV reactive material may alternatively be coated on a portion of the end effector 221. Alternatively, the UV reactive material may be coated on portions or the entire surfaces of the end effector 221 and the shaft 223. In this case, an image different from FIG. 4 may be acquired. That is, an image in which only UV reactive material-coated portions are shown may be acquired during UV radiation.

As described above, when the UV reactive material is coated only on a portion of the end effector 221 of the surgical tool 220, only the portion of the end effector 221 coated with the UV reactive material is shown in an image acquired during UV radiation. Thus, the end effector 221 may be efficiently separated from the background image.

That is, according to the illustrated embodiment, the surgical tool 220 is separated from the background image in each of a first image and a second image acquired through the camera 231 to estimate the current position and direction of the surgical tools 220 inserted into the patient P's body. In consideration of a shape and size of the surgical tool 220 separated from the background image and direction information of the camera 231, the position and direction of the surgical tool 220 may be calculated. In this regard, separation of the surgical tool 220 from the background image may be performed by using a surgical tool 220 having a specific shape, but the present embodiment is not limited thereto.

However, since the first image includes the organ 303 and the peripheral tissues 301 as well as the surgical tool 220 as illustrated in FIG. 3, an error may occur when the surgical tool 220 is separated from the background image including the organ 303 and the peripheral tissues 301. Accordingly, the second image showing only the surgical tool 220 is acquired as illustrated in FIG. 4 by radiating UV light to the surgical tool 220 coated with the UV reactive material. By using the acquired second image, the surgical tool 220 may be accurately separated from the background image.

Meanwhile, according to the illustrated embodiment, the controller 130 of the master device 100 may calculate the current position and direction of the surgical tool 220 using only the second image (FIG. 4). For example, the controller 130 of the master device 100 may also calculate the current position and direction of the surgical tool 220 using the following method.

That is, the aforementioned error occurring during estimation using the first image, in which the surgical tool 220 cannot be accurately separated from the background image, may be corrected by periodically using the second image while calculating the position and direction of the surgical tool 220 based on the first image, selected from two images acquired by the camera 231, i.e., the first image (FIG. 3) and the second image (FIG. 4). In other words, the position and direction of the surgical tool 220 are calculated based on the image acquired under visible light, while correcting the error occurring due to inaccurate separation of the surgical tool 220 from the background image by periodically using the image acquired under UV light.

In addition, the controller 130 of the master device 100 may control the image processor 133 to process the first image acquired by the camera 231, i.e., the image acquired under visible light, to display the processed image on the display unit 120. In this regard, when only UV light is radiated, such as under the condition that only the second lighting unit 235 is turned on, the controller 130 may control the display unit 120 to display the first image acquired immediately before the second lighting unit 235 is turned on. This condition may be continued until the first lighting unit 233 is turned back on, without being limited thereto. Accordingly, a user, for example, the operator S and the assistant A, may continue to observe the inside of the patient P's body even when only UV radiation is being radiated.

Figure 5:
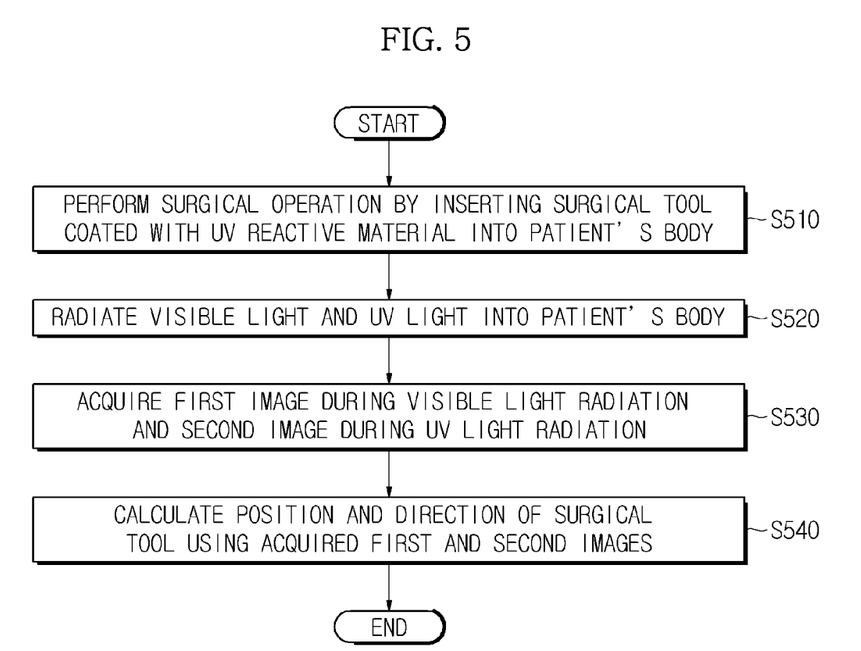
FIG. 5 is a flowchart sequentially illustrating a method of controlling a surgical robot.

FIG. 5 is a flowchart illustrating a method of controlling a surgical robot. In an embodiment, the method of controlling the surgical robot may occur sequentially as illustrated in FIG. 5, although other orders of operations may occur.

First, referring to FIGS. 1, 2, and 5, the surgical tool 220 coated with UV reactive material is inserted into the patient P's body to perform a surgical operation (S510). Here, "UV reactive material" may refer to a material that is invisible under visible light but emits visible light when exposed to UV light.

In the illustrated embodiment, the UV reactive material may be coated on the entire surface or on a portion of the surgical tool 220. In this regard, coating of the UV reactive material on the entire surface of the surgical tool 220 may refer to coating of the UV reactive material on the entire surface of the shaft and the end effector of the surgical tool 220, without being limited thereto, and may alternatively refer to coating of the UV reactive material on the entire surface of the end effector. In addition, coating of the UV reactive material on a portion of the surgical tool 220 may refer to coating of the UV reactive material on a portion of the shaft, a portion of the end effector, or portions of both the shaft and the end effector. Here, the UV reactive material may be coated to have a predetermined shape, but is not limited thereto. In addition, when the UV reactive material is coated on a portion of the surgical tool 220, a plurality of regions may be coated, but the present embodiment is not limited thereto.

Then, visible light and UV light are radiated into the patient P's body (S520).

In this case, visible light and UV light may be alternately radiated, without being limited thereto. In addition, a visible light radiation time may be longer than a UV radiation time, without being limited thereto.

Accordingly, the operator S and the assistant A performing the surgical operation may be unaware of the UV radiation. That is, the operator S and the assistant A performing the surgical operation need to thoroughly check the status of the inside of the patient P's body, and such checking may be possible only while visible light is radiated. While UV light is radiated, only the light emitting UV reactive material coated on the surgical tool 220 is visible, but organs and tissues around the surgical region of the patient P are not visible. Thus, as the UV radiation time increases, the surgical tool 220 emitting light is visible to the operator S and the assistant A, but not the organs and tissues around the surgical region and thus the status of the inside of the patient P's body cannot be checked. Accordingly, a relatively long duration of UV radiation may affect the surgical operation. Thus, the UV radiation time may be controlled to be 0.1 sec or less such that the operator S and the assistant A may be unaware of UV radiation, that is, so that the UV radiation period does not detrimentally affect the ability of the operator S and the assistant A to see the organs and tissues around the surgical region.

Meanwhile, as described above, visible light and UV light may not be alternately radiated. Instead, visible light may be periodically radiated at predetermined intervals while UV light is continuously radiated.

Particularly, visible light and UV light may be simultaneously radiated into the patient P's body, and then the first lighting unit 233 radiating visible light may be turned off for a short time period and then turned on. In this regard, a radiation-off time of the first lighting unit 233 may be shorter than a radiation-on time of the first lighting unit 233. As described above, in order to prevent the operator S and the assistant A from being aware of UV radiation, the radiation-off time may be, for example, 0.1 sec or less.

Then, a first image is acquired while visible light is radiated, and a second image is acquired while UV light is radiated (S530). That is the first image is acquired while visible light is radiated and UV light is not radiated, and a second image is acquired while UV light is radiated and visible light is not radiated.

In this regard, the first image and the second image may be acquired using the camera 231 of the slave device 200. In this regard, the camera 231 may be a stereo camera including a pair of cameras to acquire a 3D image, i.e., a left-eye camera and a right-eye camera, but is not limited thereto. According to the illustrated embodiment, the camera 231 may also be a camera that captures a visible-light image. In this regard, "visible-light image" refers to an image visible to human eyes in a visible wavelength range and may include all images acquired under visible light and under UV light according to the present embodiment.

The camera 231 may be a complementary metal-oxide semiconductor (CMOS) camera or a charge coupled device (CCD) camera, but is not limited thereto.

The first image and second image acquired according to this operation are as illustrated in FIGS. 3 and 4. That is, an organ 303, peripheral tissues 301, and the surgical tool 220 inserted into the patient P's body may be shown in the first image acquired while visible light is radiated into the patient P's body as illustrated in FIG. 3. Only the surgical tool 220 coated with the UV reactive material that emits light in response to UV radiation may be shown in the second image acquired while UV light is radiated as illustrated in FIG. 4.

As described above, the second image only displaying the surgical tool 220 is acquired by coating the surgical tool 220 with the UV reactive material and radiating UV light into the patient P's body in order to efficiently and accurately separate the surgical tool 220 from the background image during a subsequent operation.

Then, a position and direction of the surgical tool are calculated using the acquired first image and the second image (S540). Operation S54 may include the following operations.

Figure 6:
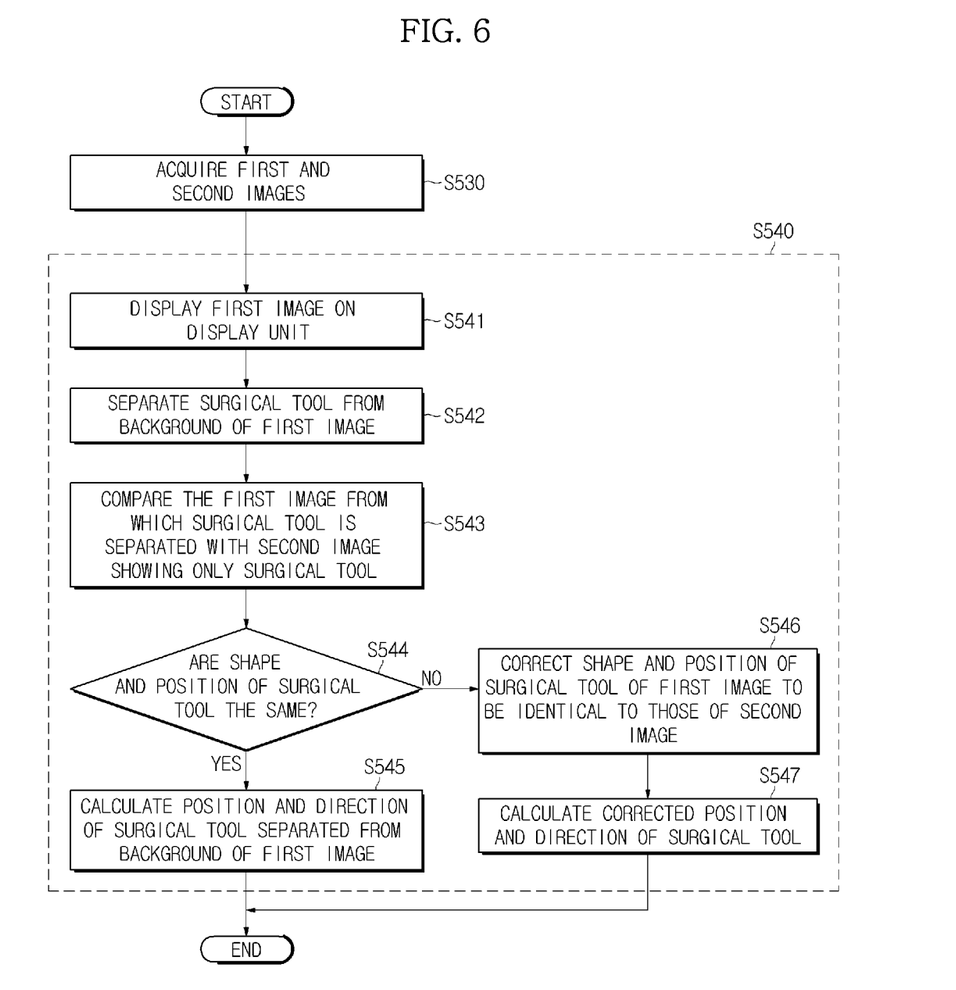
FIG. 6 is a flowchart illustrating an example of operation S540 of FIG. 5 in detail.

That is, as illustrated in FIG. 6, after the first image and the second image are acquired (S530), the first image (FIG. 3) acquired under visible light may be processed and displayed on the display unit 120 (S541). Then, the surgical tool 220 may be separated from the background image in the first image (S542), and the first image in which the surgical tool 220 is separated may be compared with the second image (FIG. 4) in which only the surgical tool 220 is displayed (S543).

Then, it may be determined whether the shape and position of the surgical tool 220 of the first image are identical to those of the surgical tool 220 of the second image (S544). When the shape and position are the same, the position and direction of the separated surgical tool 220 of the first mage may be calculated (S545). When the shape and position are not the same, the shape and position of the separated surgical tool 220 of the first image may be corrected to be identical to those of the surgical tool 220 of the second image (S546), and the position and direction of the corrected surgical tool 220 may be calculated (S547).

That is, although the position and direction of the surgical tool 220 are calculated based on the first image, an error that may occur during separation of the surgical tool 220 from the background of the first image is corrected by using the second image displaying only the surgical tool 220.

Figure 7:
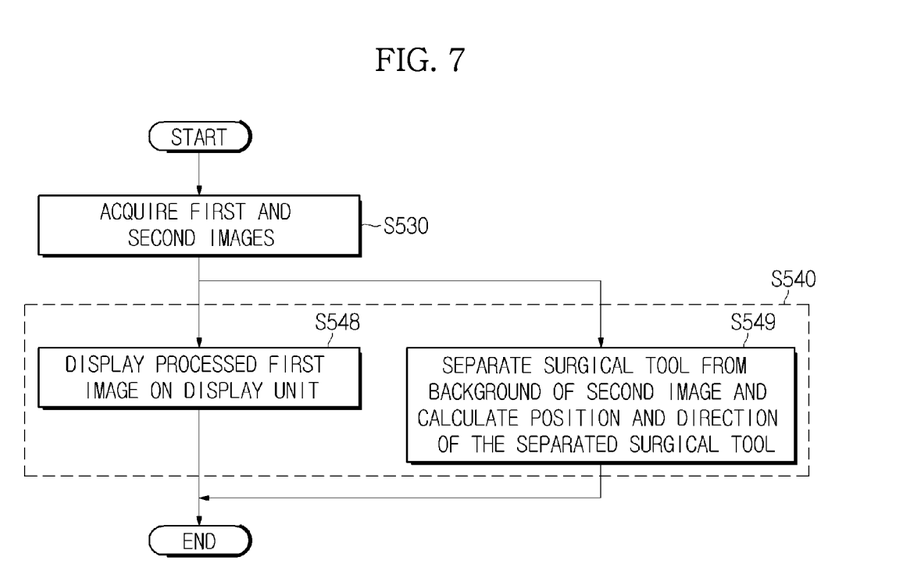
FIG. 7 is a flowchart illustrating another example of operation S540 of FIG. 5 in detail.

Meanwhile, operation S540 may be performed as illustrated in FIG. 7. Particularly, after the first image and the second image are acquired (S530), the first image (FIG. 3) acquired under visible light may be processed and displayed on the display unit 120 of the master device 100 (S541). Then, the second image (FIG. 4) in which only the surgical tool 220 acquired under UV light is displayed may be processed to separate the surgical tool 220 from the background image, and the position and direction of the separated surgical tool 220 may be calculated (S549). That is, the position and direction of the surgical tool 220 may be calculated using only the second image that displays only the surgical tool 220.

The aforementioned two methods are exemplary embodiments, and the method of calculating the position and direction of the surgical tool 220 using the first image and the second image is not limited thereto. In addition, separations of the surgical tool 220 from the background of the first image and the second image may be performed using a pre-defined shape of the surgical tool 220, without being limited thereto.

Figure 8:
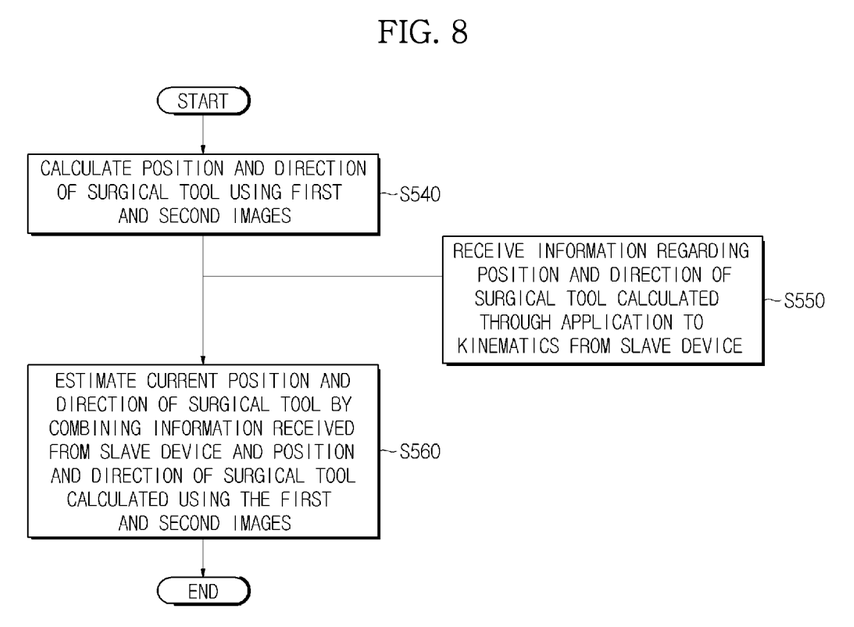
FIG. 8 is a flowchart illustrating operations performed after operation S540 of FIG. 5.

Then, referring to FIG. 8, the position and direction of the surgical tool 220 are calculated using the first image and the second image (S540). Information regarding the position and direction of the surgical tool 220 is received from the slave device 200 (S550). The final current position and direction of the surgical tool 220 may be estimated by combining information regarding the position and direction of the surgical tool 220 received from the slave device 200 and the position and direction of the surgical tool 220 calculated using the first image and the second image (S560).

In this regard, information regarding the position and direction of the surgical tool 220 received from the slave device 200 may be calculated by applying the status of motion of each joint detected by the position sensor 215 mounted on each joint of the robot arm 210 provided with the surgical tool 220 to kinematics by the position calculator 255 of the slave device 200. However, the present embodiment is not limited thereto.

As described above, the current position and direction of the surgical tool 220 may be more accurately estimated by combining the position and direction of the surgical tool 220 calculated based on kinematics by detecting the status of motion of joints of the robot arm 210 provided with the surgical tool 220 and the position and direction of the surgical tool 220 calculated using the first image and the second image in comparison with using only one method.

The methods according to the above-described example embodiments may be recorded in non-transitory computer-readable media including program instructions to implement various operations embodied by a computer. The media may also include, alone or in combination with the program instructions, data files, data structures, and the like. The program instructions recorded on the media may be those specially designed and constructed for the purposes of the example embodiments, or they may be of the kind well-known and available to those having skill in the computer software arts. The media may also include, alone or in combination with the program instructions, data files, data structures, and the like. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like.

Examples of program instructions include both machine code, such as produced by a compiler, and files containing higher level code that may be executed by the computer using an interpreter. The described hardware devices may be configured to act as one or more software modules in order to perform the operations of the above-described embodiments, or vice versa. Any one or more of the software modules described herein may be executed by a dedicated processor unique to that unit or by a processor common to one or more of the modules. The described methods may be executed on a general purpose computer or processor or may be executed on a particular machine such as the method(s) of controlling a surgical robot described herein.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A surgical robot comprising a slave device adapted to perform a surgical operation upon a patient and a master device adapted to control the surgical operation of the slave device,
wherein the slave device comprises:
an image capture unit comprising a first lighting unit to radiate visible light, a second lighting unit to radiate UV light, and a camera to capture a visible-light image; and
a surgical tool coated with a UV reactive material adapted to emit light in response to UV light radiated by the second lighting unit.

2. The surgical robot according to claim 1, wherein the master device comprises a controller to control on/off operations of the first lighting unit and the second lighting unit.

3. The surgical robot according to claim 2, wherein:
the controller controls the on/off operations of each of the first lighting unit and the second lighting unit to alternately radiate light; and
a radiation time of the first lighting unit is longer than a radiation time of the second lighting unit.

4. The surgical robot according to claim 2, wherein:
the controller controls the on/off operation of the second lighting unit to continuously emit light and the on/off operation of the first lighting unit to periodically emit light at predetermined intervals; and
the first lighting unit has a radiation-on time longer than a radiation-off time.

5. The surgical robot according to claim 2, wherein:
the visible-light image comprises a first image acquired during visible light radiation and a second image acquired during UV radiation; and
the controller receives the first image and second image from the camera and calculates a position and direction of the surgical tool using the received first image and second image.

6. The surgical robot according to claim 5, wherein the slave device further comprises:
a position sensor mounted on each joint of a robot arm provided with the surgical tool to detect status information of the joint; and
a position calculator calculating the position and direction of the surgical tool using the status information of the joint detected by the position sensor,
wherein the controller receives information regarding the calculated position and direction of the surgical tool from the slave device and estimates a current position and direction of the surgical tool by combining the received information and the position and direction of the surgical tool calculated using the first image and the second image.

7. The surgical robot according to claim 5, wherein the controller receives the first image and the second image from the camera, separates the surgical tool from a background of the received first image through image processing, determines whether a shape and the position of the surgical tool of the first image in which the surgical tool is separated are identical to a shape and position of the surgical tool of the second image, and calculates the position and direction of the separated surgical tool of the first image when the shape and position are the same, or corrects the shape and position of the surgical tool of the first image to be identical to the shape and position of the surgical tool of the second image and calculates a position and direction of the surgical tool of the corrected first image when the shape and position are not the same.

8. The surgical robot according to claim 5, wherein:
the master device comprises a display unit to display the first image; and
the controller processes the first image and outputs the processed image to the display unit.

9. The surgical robot according to claim 8, wherein the controller outputs the first image acquired immediately before the second lighting unit is turned on to the display unit while only the second lighting unit is turned on.

10. The surgical robot according to claim 1, wherein:
the UV reactive material is coated on a portion of the surgical tool; and the coated UV reactive material has a predetermined shape.

11. The surgical robot according to claim 1, wherein:
the UV reactive material is coated on a plurality of portions of the surgical tool.

12. The surgical robot according to claim 1, wherein the UV reactive material is coated on an entire surface of the surgical tool.

* * * * *